United States Patent
Kamal et al.

(10) Patent No.: US 11,324,625 B1
(45) Date of Patent: May 10, 2022

(54) INTERNAL NASAL SPLINT

(71) Applicant: GIFTEDNESS AND CREATIVITY COMPANY, Safat (KW)

(72) Inventors: Mohammad A Kh H Kamal, Safat (KW); Abdulmohsen E A H Al-Terki, Safat (KW)

(73) Assignee: GIFTEDNESS AND CREATIVITY COMPANY, Safat (KW)

( * ) Notice: Subject to any disclaimer, the term of this patent is extended or adjusted under 35 U.S.C. 154(b) by 0 days.

(21) Appl. No.: 17/461,931

(22) Filed: Aug. 30, 2021

Related U.S. Application Data

(60) Provisional application No. 63/212,665, filed on Jun. 20, 2021.

(51) Int. Cl.
*A61F 5/08* (2006.01)
*A61M 31/00* (2006.01)

(52) U.S. Cl.
CPC ............... *A61F 5/08* (2013.01); *A61M 31/00* (2013.01); *A61M 2210/0618* (2013.01)

(58) Field of Classification Search
CPC ........ A61F 2/18; A61F 13/2005; A61F 2/186; A61B 17/24; A61B 17/12104; A61M 2210/0618; A61M 16/0666; A61M 15/08; A61M 2210/0681
See application file for complete search history.

(56) References Cited

U.S. PATENT DOCUMENTS

| | | | | | |
|---|---|---|---|---|---|
| 3,903,893 | A | * | 9/1975 | Scheer | A61B 17/12104 606/196 |
| 3,935,859 | A | * | 2/1976 | Doyle | A61F 5/05891 606/196 |
| 4,338,941 | A | * | 7/1982 | Payton | A61B 17/12104 606/199 |
| 4,592,357 | A | * | 6/1986 | Ersek | A61F 5/08 606/199 |
| 4,606,346 | A | * | 8/1986 | Berg | A61F 5/34 606/196 |
| 4,950,280 | A | * | 8/1990 | Brennan | A61B 17/12022 604/1 |
| 5,350,396 | A | * | 9/1994 | Eliachar | A61F 5/08 602/17 |
| 5,601,594 | A | * | 2/1997 | Best | A61F 5/08 606/196 |

(Continued)

*Primary Examiner* — Adam Marcetich
(74) *Attorney, Agent, or Firm* — Nath, Goldberg & Meyer; Richard C. Litman

(57) ABSTRACT

The internal nasal splint is used in pairs, one on each side of the septum, to support the septum, maintain patent airways on each side of the septum, and reduce or mitigate the incidence of hematomas and post-surgical adhesions following such nasal surgeries as septoplasty, removal of nasal polyps, correction of nasal fractures, etc. The two splints are symmetrical, and each includes an arcuate septal support splint portion defining a delivery lumen or tube having a plurality of medially spaced delivery ports or orifices, and a lateral flared splint portion defining an airway passage extending between the opening of the nostril and the internal nasal valve, the two splint portions being joined by an isthmus or bridge. A suture access pad is provided on each internal nasal splint to facilitate suturing the splints to the septum when placing the splints in the corresponding naris or nostril during the surgery.

14 Claims, 4 Drawing Sheets

(56) References Cited

U.S. PATENT DOCUMENTS

| | | | | |
|---|---|---|---|---|
| 5,827,224 | A * | 10/1998 | Shippert | A61M 1/67 604/523 |
| 10,857,023 | B1 * | 12/2020 | Hogle | A61F 5/08 |
| 2004/0243172 | A1 * | 12/2004 | Hogle | A61B 17/24 606/199 |
| 2009/0120441 | A1 * | 5/2009 | Wang | A61M 15/085 128/206.11 |
| 2009/0248058 | A1 * | 10/2009 | Kotler | A61F 5/08 606/199 |
| 2009/0250067 | A1 * | 10/2009 | Beck Arnon | A61M 15/08 128/207.18 |
| 2010/0121308 | A1 * | 5/2010 | Muni | A61B 5/064 604/514 |
| 2012/0010647 | A1 * | 1/2012 | Pylyp | A61F 5/08 606/199 |
| 2013/0213411 | A1 * | 8/2013 | Tamez | A61F 5/05891 128/858 |
| 2014/0216449 | A1 * | 8/2014 | Chang | A61M 16/0409 128/202.16 |
| 2014/0276626 | A1 * | 9/2014 | Jenkins | A61M 3/0279 604/514 |
| 2016/0166421 | A1 * | 6/2016 | Atkins | A61F 5/05891 606/204.45 |
| 2019/0282443 | A1 * | 9/2019 | Wu | A61M 25/007 |
| 2021/0077383 | A1 * | 3/2021 | Reitz | A61K 9/0043 |
| 2021/0085940 | A1 * | 3/2021 | Kozlov | A61M 31/00 |

\* cited by examiner

INTERNAL NASAL SPLINT

CROSS REFERENCE TO RELATED APPLICATIONS

This application claims priority to U.S. Provisional Patent Application Ser. No. 63/212,665, filed Jun. 20, 2021.

BACKGROUND

1. Field

The present disclosure relates to nasal splints, and particularly to an internal nasal splint that has both an integral air tube for maintaining a patent airway and an integral delivery tube for delivery of intranasal medications.

2. Description of the Related Art

Many nasal surgeries entail the use of nose or nasal splints as an element of post-surgical treatment to reduce the incidence and/or the severity of post-surgical complications, such as unintentional shifts in the position of the septum from trauma or abnormal pressure, excessive bleeding or collection of blood (hematoma) in the tissues, maintaining patency of the nasal airways, etc. These nasal surgeries include rhinoplasty, septoplasty, removal of nasal polyps, correction of nasal fractures, etc. For rhinoplasty, the doctor or surgeon will typically apply external splints, which may be secured by bandages, adhesive tape, or a temporary skin adhesive that will keep the splints in place long enough to keep the septum straight until the nasal cartilage has knitted sufficiently to maintain the shape and position of the septum without the need for external support.

When the nasal surgery is for septoplasty, removal of nasal polyps, or correction of nasal fractures, many surgeons routinely put in internal nasal splints as part of the procedure in the belief that placement of the splints will stabilize the healing septum, apply compression to the septum to mitigate postoperative bleeding and prevent the formation of hematomas, and reduce postoperative nasal adhesions. Two internal splints are placed, one for each nostril. The splints are typically plastic tubes made of a biocompatible plastic, such as silicone, having some degree of flexibility but retaining sufficient stiffness to protect the cartilage of the septum from accidental deviation while the tissue heals and maintain the airway tube open between the nostril opening and the opening of the nasal passages to the nasopharynx and the sinuses. The splints are secured to the septum by one or two stitches, and are removed by the doctor or surgeon, often within two days to one week for uncomplicated procedures, or in about two weeks for more complicated reconstructions. Doyle splints or modifications thereof are commonly used.

While such internal nasal splints are usually satisfactory for many patients, some patients may require the intranasal topical or inhalation administration of medications of the tissues of the septum for treatment of post-surgical complications, e.g., infections. This may be difficult or impossible to accomplish without removal and subsequent surgical replacement of conventional internal nasal splints. Thus, an internal nasal splint solving the aforementioned problems is desired.

SUMMARY

The internal nasal splint is used in pairs, one on each side of the septum, to support the septum, maintain patent airways on each side of the septum, and reduce or mitigate the incidence of hematomas and post-surgical adhesions following such nasal surgeries as septoplasty, removal of nasal polyps, correction of nasal fractures, etc. The two splints are symmetrical, and each includes an arcuate septal support splint portion defining a delivery lumen or tube having a plurality of medially spaced delivery ports or orifices, and a lateral flared splint portion defining an airway passage extending between the opening of the nostril and the internal nasal valve, the two splint portions being joined by an isthmus or bridge. A suture access pad is provided on each internal nasal splint to facilitate suturing the splints to the septum when placing the splints in the corresponding naris or nostril during the surgery.

Thus, the internal nasal splint provides the capability of delivering medication to the septum intranasally without interfering with maintaining patency of the airways without the necessity of removing and replacing the splints during the healing period immediately following nasal surgeries involving reconstruction of the septum. The splints may be made in a variety of sizes and shapes so that they may be custom-fitted to the patient at the time of surgery. The splints may be furnished in kit form with at least one syringe fitted with a catheter or flexible delivery tube configured for insertion into the delivery lumens of the corresponding nasal splints for post-surgical deliver of medication to the septum.

These and other features of the present subject matter will become readily apparent upon further review of the following specification. and drawings

BRIEF DESCRIPTION OF THE DRAWINGS

Similar reference characters denote corresponding features consistently throughout the attached drawings.

DETAILED DESCRIPTION OF THE PREFERRED EMBODIMENTS

The internal nasal splint is used in pairs, one on each side of the septum, to support the septum, maintain patent airways on each side of the septum, and reduce or mitigate the incidence of hematomas and post-surgical adhesions following such nasal surgeries as septoplasty, removal of nasal polyps, correction of nasal fractures, etc. The two splints are symmetrical, and each includes an arcuate septal support splint portion defining a delivery lumen or tube having a plurality of medially spaced delivery ports or orifices, and a lateral flared splint portion defining an airway passage extending between the opening of the nostril and the internal nasal valve, the two splint portions being joined by an isthmus or bridge. A suture access pad is provided on each internal nasal splint to facilitate suturing the splints to the septum when placing the splints in the corresponding naris or nostril during the surgery.

Thus, the internal nasal splint provides the capability of delivering medication to the septum intranasally without interfering with maintaining patency of the airways without the necessity of removing and replacing the splints during the healing period immediately following nasal surgeries involving reconstruction of the septum. The splints may be made in a variety of sizes and shapes so that they may be custom-fitted to the patient at the time of surgery. The splints may be furnished in kit form with at least one syringe fitted with a catheter or flexible delivery tube configured for insertion into the delivery lumens of the corresponding nasal splints for post-surgical deliver of medication to the septum.

Figure 1A:
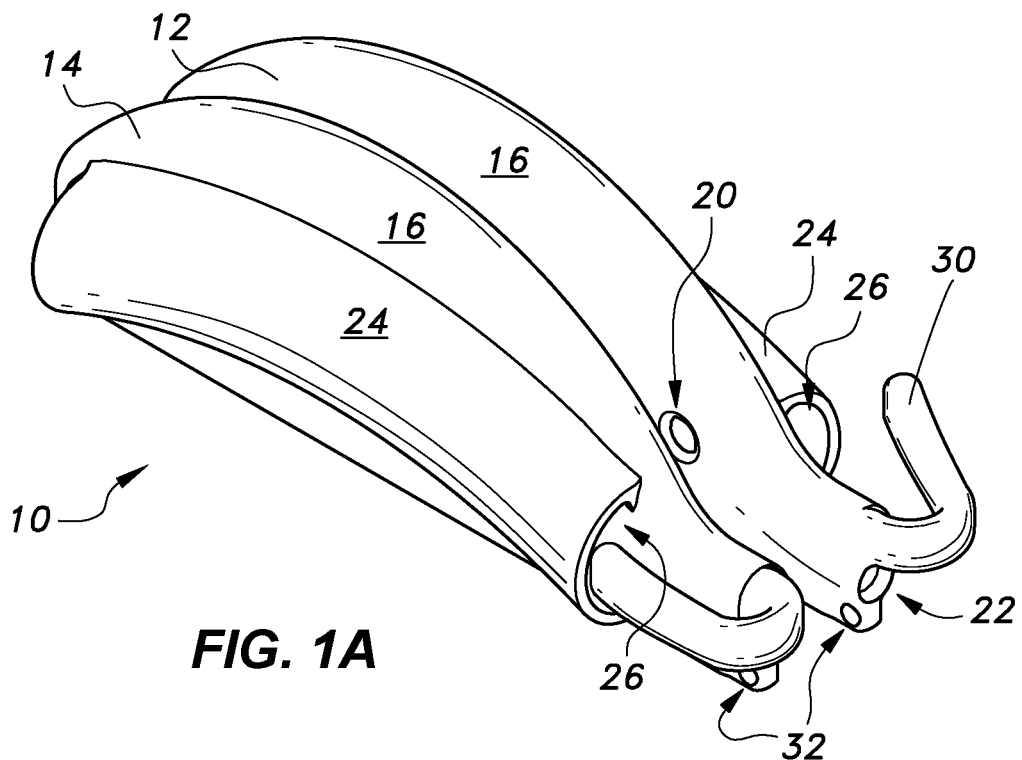
FIG. 1A is a perspective view of a pair of internal nasal splints.
Figure 1B:
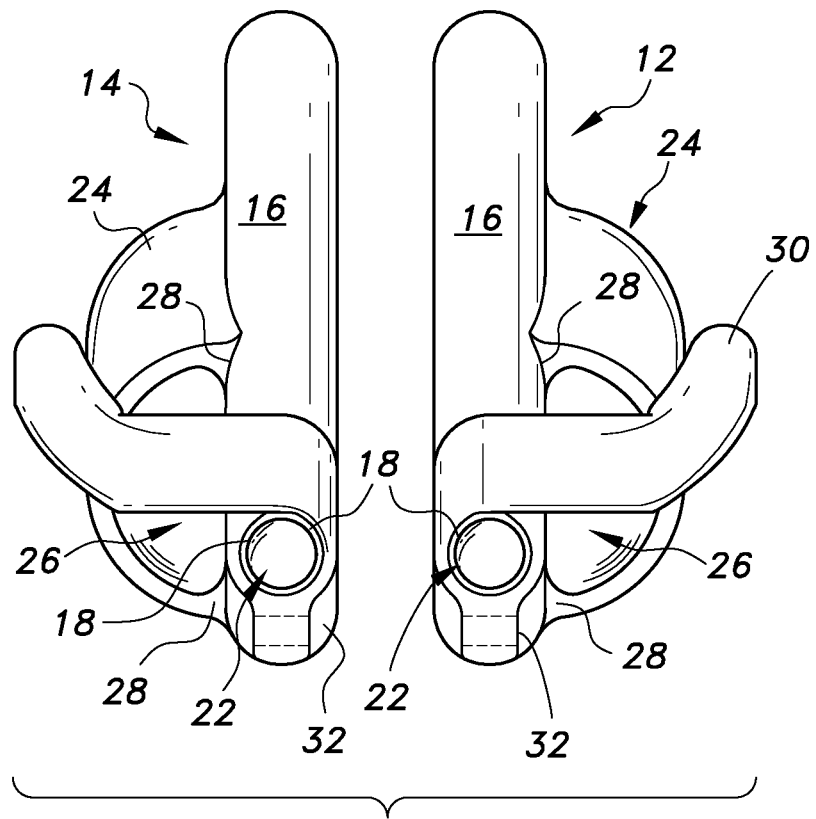
FIG. 1B is front view of the pair of internal nasal splints of FIG. 1.

As described above and shown in FIGS. 1A and 1B, the internal nasal splint 10 is used in pairs, including a first splint 12 adapted for placement in the left nostril and a symmetrical second splint 14 adapted for placement in the right nostril. Each of the splints 12, 14 has an arcuate septal support splint portion 16 defining a delivery lumen or tube 18 (shown more clearly in FIGS. 3B and 3C) having a plurality of medially spaced delivery ports or orifices 20 adapted for delivery of medication to the septum as needed. The delivery lumen or tube 18 has an inlet opening 22 adapted for introduction of the medication in the anterior end of the corresponding splint 12, 14, the lumen or tube 18 extending from the anterior end of the splint 12, 14 to the posterior end. The body of the septal splint portion 16 is somewhat arcuate or parabolic, being dimensioned and configured to conform closely to the cartilage forming the septum from the nostril opening to the internal nasal valve and internal nasal passages.

Figure 2A:
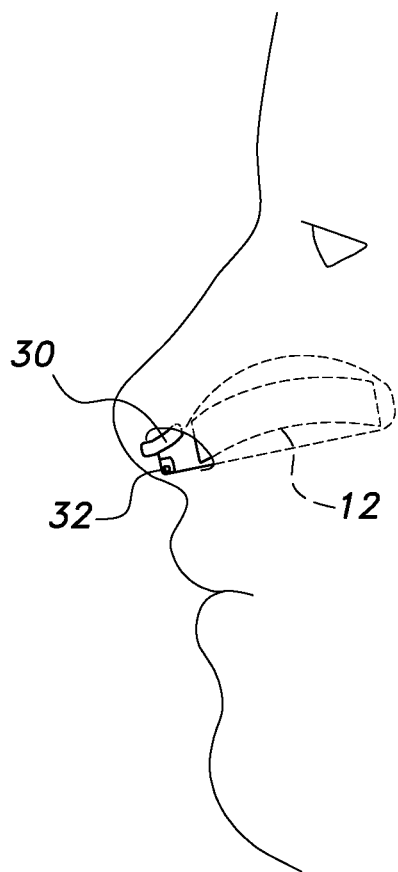
FIG. 2A is an environmental side view of a patient having an internal nasal splint placed in the patient's nose.
Figure 2B:
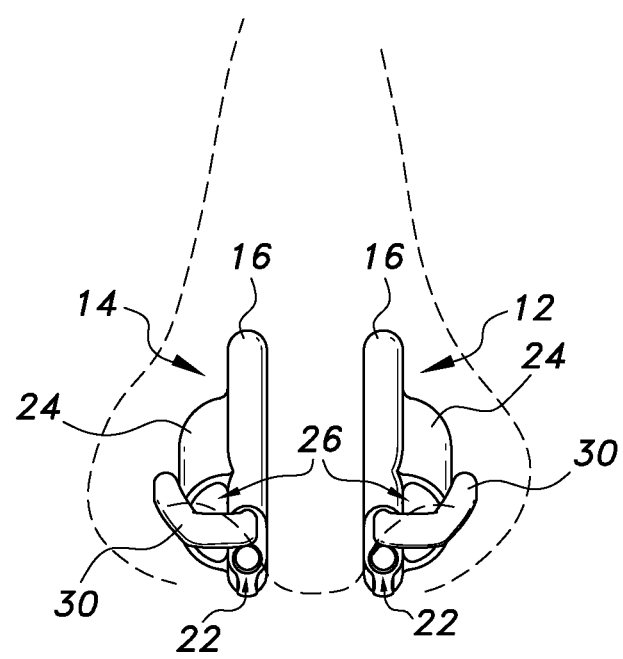
FIG. 2B is an environmental front view of a pair of internal nasal splints placed in a patient's nose.

Each of the splints 12, 14 also has a lateral flared splint portion 24 defining an airway passage 26 extending between the opening of the nostril and the internal nasal valve. The lateral flared splint portion 24 ensures that the cartilage of the nostril or external nasal valve will retain proper shape during healing and will not collapse, thereby maintaining an open airway passage for breathing. The septal support splint portion 16 and the lateral flared splint portion 24 may be made from slightly different blends of plastic material, the septal support splint portion 16 being somewhat more flexible to conform to the septum and the lateral flared splint portion 24 being more rigid to maintain the shape of the lateral cartilage, the two portions 16, 24 being joined by an isthmus 28 of suitable material, as known in the plastics manufacturing art. The septal support splint portion 16 may have a hook portion 30 extending anteriorly for engaging the patient's nose, as shown in FIG. 2B, to retain the splints 12, 14 in the nose and prevent accidental inhalation or swallowing of the splints 12, 14. Each of the splints 12, 14 has a suture opening or suture pad 32 defined in the anterior tip of the septal support splint portion 16 so that the splints 12, 14 may be secured to the anterior tip of the septum during the early portion of the post-surgical healing period.

Figure 3A:
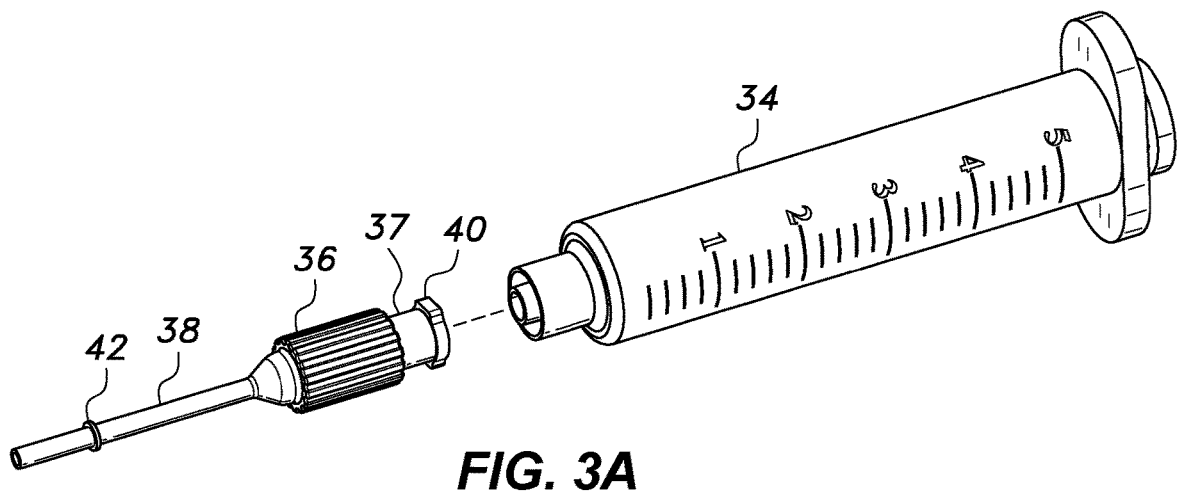
FIG. 3A is a perspective view of a syringe that may be used for delivery of medications through the delivery tube of the internal nasal splint into the patient's nose.
Figure 3B:
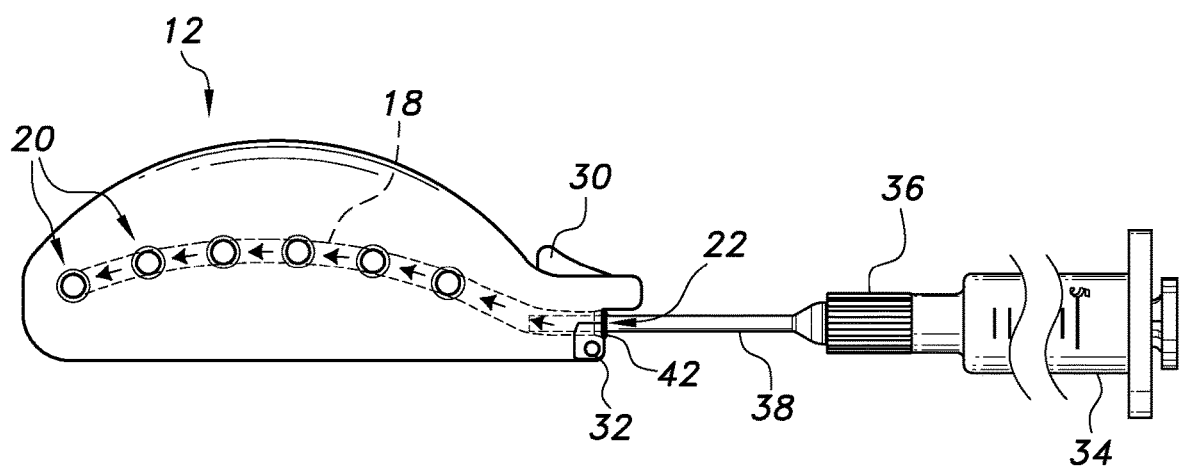
FIG. 3B is side view of components of an internal nasal splint kit, showing the path for delivery of medication through one of the splints.
Figure 3C:
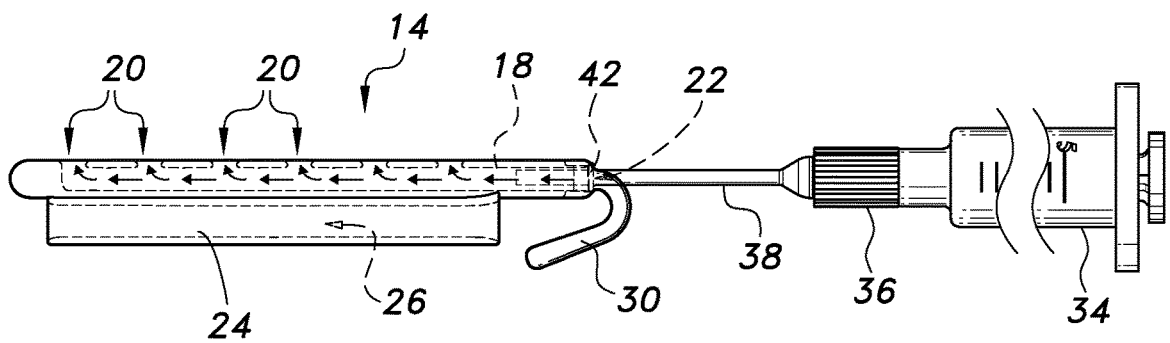
FIG. 3C is a top view of components of an internal nasal splint kit, showing the path for delivery of medication through one of the splints.

The internal nasal splint 10 may be provided in the form of a kit including a first splint 12 adapted for placement in the left nostril, a symmetrical second splint 14 adapted for placement in the right nostril, and a syringe for delivery of medication through the delivery lumen or tube 18. FIG. 3A shows an exemplary syringe 34 that may be included in such a kit. The syringe 34 includes an adapter 36 having a hub 37 and a catheter or delivery tube 38 extending from the hub 37, the adapter 36 being attachable to the barrel of the syringe 34 by a male Luer lock connector 40 attachable to a corresponding female Luer lock connector at the bottom of the barrel of the syringe 34. the catheter 38 being dimensioned and configured for insertion into the opening 22 of the delivery lumen or tube 18 for injecting or spraying medications in liquid form, which are distributed to the tissue of the septum through a series of spaced delivery ports 20 defined medially in the delivery lumen or tube 18. The catheter or delivery tube 38 may have an annular stop 42 that may temporarily seal the inlet opening 22 of the delivery lumen or tube 18 when abutted against the inlet opening 22 to deliver the medication, as shown in FIG. 3B. The splints 12, 14 may be prefabricated in a variety of sizes and shapes so that the internal nasal splint may be pre-fitted to the patient at the time of surgery.

The provision of symmetrical splints 12, 14, each including a septal support splint portion 16 defining a delivery lumen or tube 18 integral with a lateral flared portion 24 defining an air passageway 26 enables the delivery of medication to the septum for treatment of pre-surgical or post-surgical conditions or complications without interfering with maintenance of an airway for breathing for patients undergoing nasal surgeries involving septal reconstruction, which is not currently available.

Figure 4:
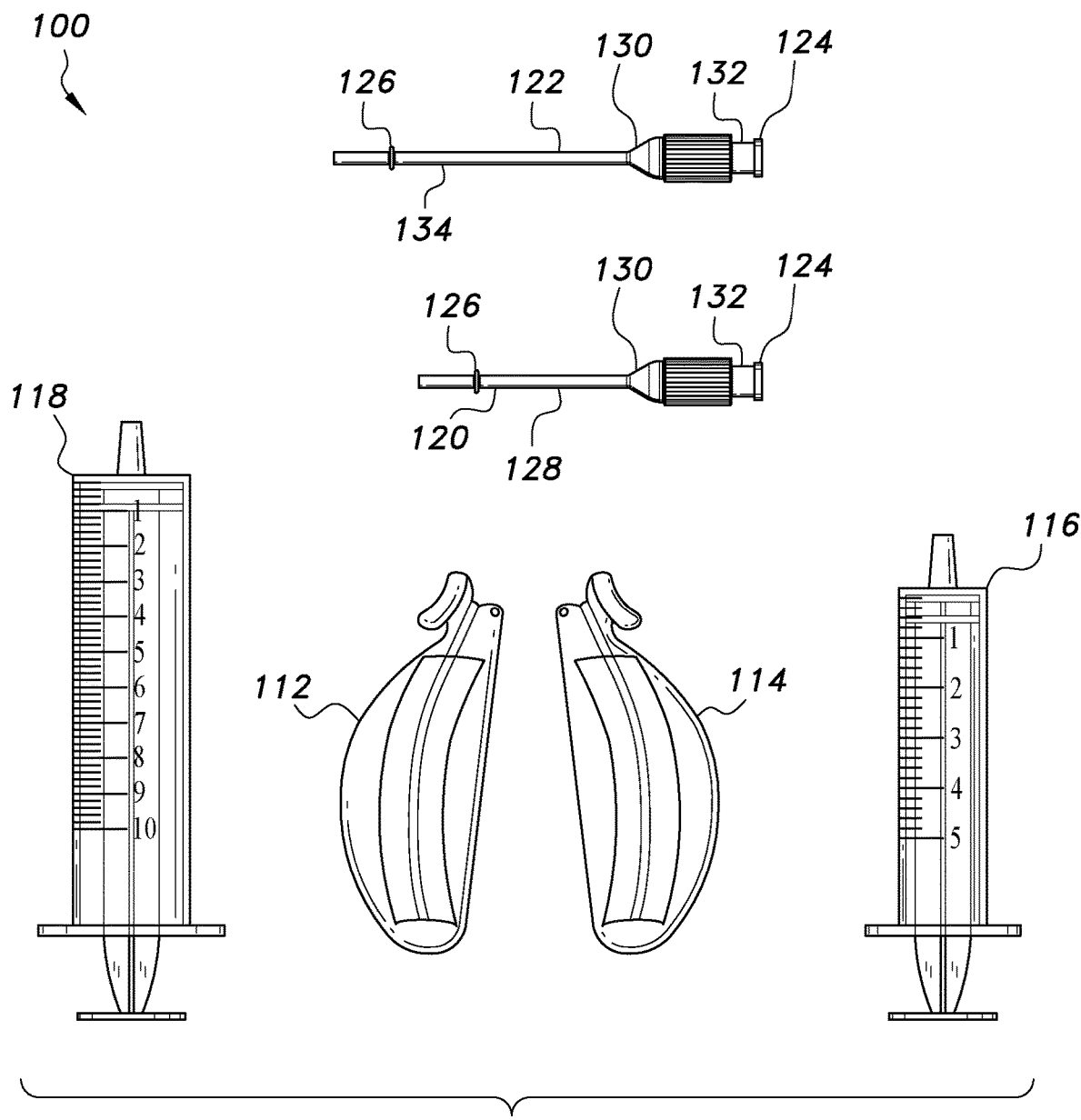
FIG. 4 is a front view of an internal nasal splint kit.

Although the internal nasal splint has been described as being useful following surgeries involving septal reconstruction, the internal nasal splint can also be used in the outpatient department or emergency room to treat patients with epistaxis (nose bleeds), nasal infections, post nasal trauma, and other conditions where daily insertions of medications is needed. The internal nasal splint may be stocked in different sizes, and one or both of the symmetrical splints 12, 14 may be placed and fixed under local anesthesia. FIG. 4 shows an exemplary configuration of an internal nasal splint kit 100 that expands the functionality of the splints.

The kit 100 includes at least one pair of the symmetrical splints, including a first splint 112 for the left nostril and a second splint 114 for the right nostril. The kit of FIG. 4 includes two syringes of different volumes, including a small 5 ml syringe 116 and a larger 10 ml syringe 118. The kit of FIG. 4 also includes two different adapters 120, 122 of different length. Each adapter 120, 122 has a male Luer lock connector 124 for attaching the adapter to a corresponding female Luer lock connector below the barrel of one of the syringes 116, 118, and a catheter or delivery tube having an annular stop 126 close to the nozzle or discharge end. The shorter adapter 120 may have a delivery tube 128 measuring, for example, 20.4 mm from the distal end 130 of the hub 132 to the stop 126, while the longer adapter 122 may have a delivery tube 134 measuring, for example, 70.2 mm from the distal end 130 of the hub 132 to the stop 126.

The shorter adapter 120 may be used for administering medications through the inlet opening 22 of the delivery lumen or tube 18 of the corresponding internal nasal splint 12, 14, 112, or 114. The longer adapter 122 may be used for administering medication either through one of the internal nasal splints 12, 14, 112, or 114, or directly inside the nasal cavity without the use of a splint, if needed to introduce medications in the nasal cavity outside the internal nasal splint, where it can be used any place in the nasal cavity, including all the way to the back of the nasal cavity due to its extended length.

It is to be understood that the internal nasal splint is not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An internal nasal splint, comprising a body of biocompatible plastic material adapted for placement within a patient's nose during a surgery involving reconstruction of the nasal septum, the body having an anterior end, a posterior end, a medial side, and a lateral side, the body including:
   a septal support splint portion dimensioned and configured for supporting and maintaining shape of the septum during post-surgical healing, the septal support splint portion defining a delivery lumen extending from the anterior end to the posterior end, the delivery lumen having an opening at the anterior end and a plurality of spaced apart delivery ports on the medial side, the delivery lumen being adapted for delivery of medication to the septum; and
   a lateral flared splint portion attached to and integral with the lateral side of the septal support portion, the lateral flared splint portion being dimensioned and configured for maintaining the external nasal valve open and defining an air passage extending from the nostril opening of the nose at least to the internal nasal valve;
   whereby the internal nasal splint permits delivery of medication to the septum without interference with the passage of air through the nose while the splint is positioned within the nose during post-surgical healing.

2. The internal nasal splint according to claim 1, wherein said septal support splint portion is an arcuate body for closely conforming to cartilage of the septum.

3. The internal nasal splint according to claim 1, wherein said septal support splint portion and said lateral flared splint portion have different compositions, said septal support splint portion being more flexible than said lateral flared splint portion to approximate the septum and said lateral flared splint portion being more rigid than said septal support splint portion to maintain the external nasal valve open.

4. The internal nasal splint according to claim 1, wherein the internal nasal splint is configured for placement on the left side of the nasal septum.

5. The internal nasal splint according to claim 4, further comprising a second internal nasal splint symmetrical to the internal nasal splint of claim 4, the second internal nasal splint being configured for placement on the right side of the nasal septum.

6. The internal nasal splint according to claim 1, wherein said septal support splint portion has a suture opening defined in the anterior end adapted for securing the internal nasal splint to the septum by at least one suture.

7. The internal nasal splint according to claim 1, wherein said septal support splint portion further comprises a hook portion extending laterally from the anterior end, the hook portion being adapted for engaging a nostril of the nose to prevent the internal nasal splint from shifting position too far into the nasal cavity.

8. An internal nasal splint kit, comprising:
   a first internal nasal splint according to claim 1 configured for placement on the left side of the nasal septum;
   a second internal nasal splint according to claim 1, the second internal nasal splint being symmetrical to the first nasal splint and configured for placement on the right side of the nasal septum; and
   a syringe for delivery of medication, the syringe having a barrel end, an adapter removably attached to the barrel end, and a catheter extending from the adapter, the catheter being dimensioned and configured for insertion into the opening in the anterior end of the delivery lumen for injecting the medication into the delivery lumen.

9. An internal nasal splint kit, comprising:
   a first internal nasal splint having a body of biocompatible plastic material adapted for placement within a patient's nose during a surgery involving reconstruction of the nasal septum, the body having an anterior end, a posterior end, a medial side, and a lateral side, the body including:
      a septal support splint portion dimensioned and configured for supporting and maintaining shape of the septum during post-surgical healing, the septal support splint portion defining a delivery lumen extending from the anterior end to the posterior end, the delivery lumen having an opening at the anterior end and a plurality of spaced apart delivery ports on the medial side, the delivery lumen being adapted for delivery of medication to the septum; and
      a lateral flared splint portion attached to an integral with the lateral side of the septal support portion, the lateral flared splint portion being dimensioned and configured for maintaining the external nasal valve open and defining an air passage extending from the nostril opening of the nose at least to the internal nasal valve, the first internal nasal splint being configured for placement on the left side of the nasal septum;
   a second internal nasal splint symmetrical to the first internal nasal splint, the second internal nasal splint being configured for placement on the right side of the nasal septum; and
   at least one syringe for delivery of medication, the at least one syringe having a barrel end; and
   at least one adapter removably attached to the barrel end of the at least one syringe, the at least one adapter having a delivery tube extending from the adapter.

10. The internal nasal splint kit according to claim 9, wherein said at least one syringe comprises two syringes having different volume capacities.

11. The internal nasal splint kit according to claim 9, wherein said at least one syringe comprises a first syringe having a five milliliter capacity and a second syringe having a ten milliliter capacity.

12. The internal nasal splint kit according to claim 9, wherein said at least one adapter comprises a hub having a proximal end defining an opening into the hub, a male Luer lock connector disposed at the proximal end of the hub adapted for releasable attachment to a female Luer lock connector on a barrel end of said at least one syringe, and a distal end having a delivery tube extending therefrom for delivering medication from said at least one syringe into the nose.

13. The internal nasal splint kit according to claim 12, wherein the delivery tube of said at least one adapter further comprises an annular stop disposed around the delivery tube, the annular stop being dimensioned and configured for limiting insertion of the delivery tube into one of the internal nasal splints and temporarily sealing the opening into the delivery lumen while administering medication into the patient's nose through the internal nasal splint.

14. The internal nasal splint kit according to claim 13, wherein said at least one adapter comprises a second adapter having a length greater than a first adapter measured from the distal end of the hub to the stop, the first adapter being dimensioned and configured for insertion into the opening in the anterior end of the delivery lumen for injecting the medication into the delivery lumen of one of the internal splints, the second adapter being dimensioned and configured for insertion into the opening in the anterior end of the delivery lumen for injecting the medication into the delivery lumen of one of the internal splints and optionally for administering medication anywhere in the patient's nasal cavity without use of the internal nasal splints.

\* \* \* \* \*